(12) United States Patent
Akiyama Da Cruz et al.

(10) Patent No.: US 12,011,260 B2
(45) Date of Patent: Jun. 18, 2024

(54) HIGH-RESOLUTION PORTABLE BIOMETRIC READER FOR NEWBORNS

(71) Applicants: SERVICO NACIONAL DE APRENDIZAGEM INDUSTRIAL, Salvador (BR); NATOSAFE TECNOLOGIA DA INFORMAÇÃO S/A, Curitiba (BR)

(72) Inventors: Ismael Akiyama Da Cruz, Pinhais (BR); Thais Gualda Carneiro Akiyama, Pinhais (BR); Valéria Loureiro Da Silva, Lauro de Freitas (BR); Valmara Silveira Ponte, Salvador (BR); Felipe Cafezeiro Plech, Lauro de Freitas (BR); Antônia Larissa Reis Barbosa, Salvador (BR); Vitor Alberto Nascimento Souza, Salvador (BR); Fabio De Oliveira Condurú Ferreira, Salvador (BR)

(73) Assignees: SERVICO NACIONAL DE APRENDIZAGEM INDUSTRIAL, Salvador (BR); NATOSAFE TECNOLOGIA DA INFORMAÇÃO S/A, Curitiba (BR)

( * ) Notice: Subject to any disclaimer, the term of this patent is extended or adjusted under 35 U.S.C. 154(b) by 132 days.

(21) Appl. No.: 17/635,221

(22) PCT Filed: Aug. 14, 2020

(86) PCT No.: PCT/BR2020/050324
§ 371 (c)(1),
(2) Date: Mar. 25, 2022

(87) PCT Pub. No.: WO2021/026627
PCT Pub. Date: Feb. 18, 2021

(65) Prior Publication Data
US 2022/0218234 A1    Jul. 14, 2022

(30) Foreign Application Priority Data

Aug. 14, 2019    (BR) .......................... 1020190168986

(51) Int. Cl.
*A61B 5/1172*    (2016.01)
*G02B 6/42*    (2006.01)
*G06F 1/16*    (2006.01)

(52) U.S. Cl.
CPC .......... *A61B 5/1172* (2013.01); *G02B 6/4214* (2013.01); *G06F 1/1613* (2013.01)

(58) Field of Classification Search
CPC ... A61B 5/1172; A61B 5/0082; A61B 5/6887; A61B 2503/045; A61B 2562/0233;
(Continued)

(56) References Cited

U.S. PATENT DOCUMENTS 8,175,346 B2    5/2012    Rowe et al.
2005/0169506 A1    8/2005    Fenrich et al.

OTHER PUBLICATIONS

International Search Report and Written Opinion for PCT/BR2020/050324, mailed Sep. 30, 2020.
(Continued)

*Primary Examiner* — Abhishek Sarma
(74) *Attorney, Agent, or Firm* — Renner, Otto, Boisselle & Sklar, LLP

(57) ABSTRACT

The present patent of invention describes a high-resolution portable biometric reader for newborns that, according to the characteristics thereof, provides for the creation of a biometric reader for newborns (1) in a curved portable structure of electronic type and based on a frame and a comfortable handle enabling the operator to hold the reader in a single hand and arrange the capture surface area according to the newborn's position thus enabling the fingerprints of the newborn and those of the mother to be digitally captured using the frustrated total internal reflection technique with a (Continued)

prism as an optical system (4) having a resolution greater than 29 lp/mm (1450 ppi) over the entire capture area of more than 18×36 mm, so as to provide full optimization in the capturing procedures for fingerprint, palm-print and footprint imaging of newborn babies and the fingerprints of the respective mothers, i.e., the simultaneous registration of the fingerprints of both the baby and the mother and the subsequent inclusion in a medical register system to improve record tracking.

1 Claim, 12 Drawing Sheets

(58) Field of Classification Search
CPC ... A61B 5/1174; G02B 6/4214; G06F 1/1613; G06V 10/17; G06V 40/1318; G06V 40/1324; G16H 40/20; G16H 40/63; G16H 30/40; H04L 9/3231
See application file for complete search history.

(56) References Cited

OTHER PUBLICATIONS

Daniel Weingaertner et al., "Newborn's Biometric Identification: Can It Be Done?" Proceedings of the Third International Conference on Computer Vision Theory and Applications, VISAPP 2008, Jan. 2008, vol. 1.
Steven Saggese et al., "Biometric identification of newborns and infants by non-contact fingerprinting: lessons learned," Gates Open Research, May 29, 2019, 3:1477.
Yoshinori Koda et al., "Advances in capturing child fingerprints: a high resolution CMOS image sensor with SLDR method," BIOSIG, Sep. 2016.
Anil K. Jain et al., "Fingerprint Recognition of Young Children," IEEE Transactions on Information Forensics and Security, Jul. 2017, pp. 1,501-1,514, vol. 12, No. 7.
Emmanuelle Honore et al., Hand measurement data from human babies at birth, from 26 to 41 weeks estimated gestational age, Data in Brief, Apr. 2016, pp. 1,451-1,454, vol. 7.

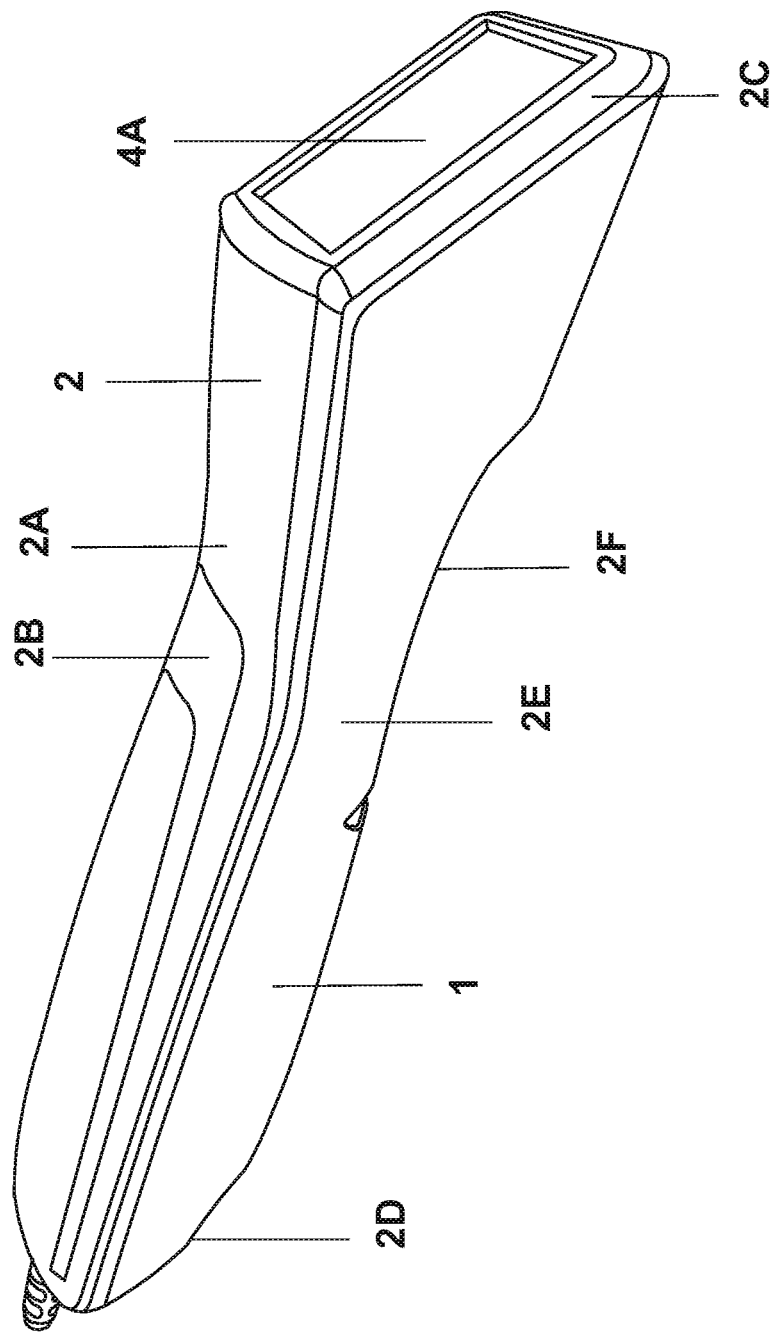

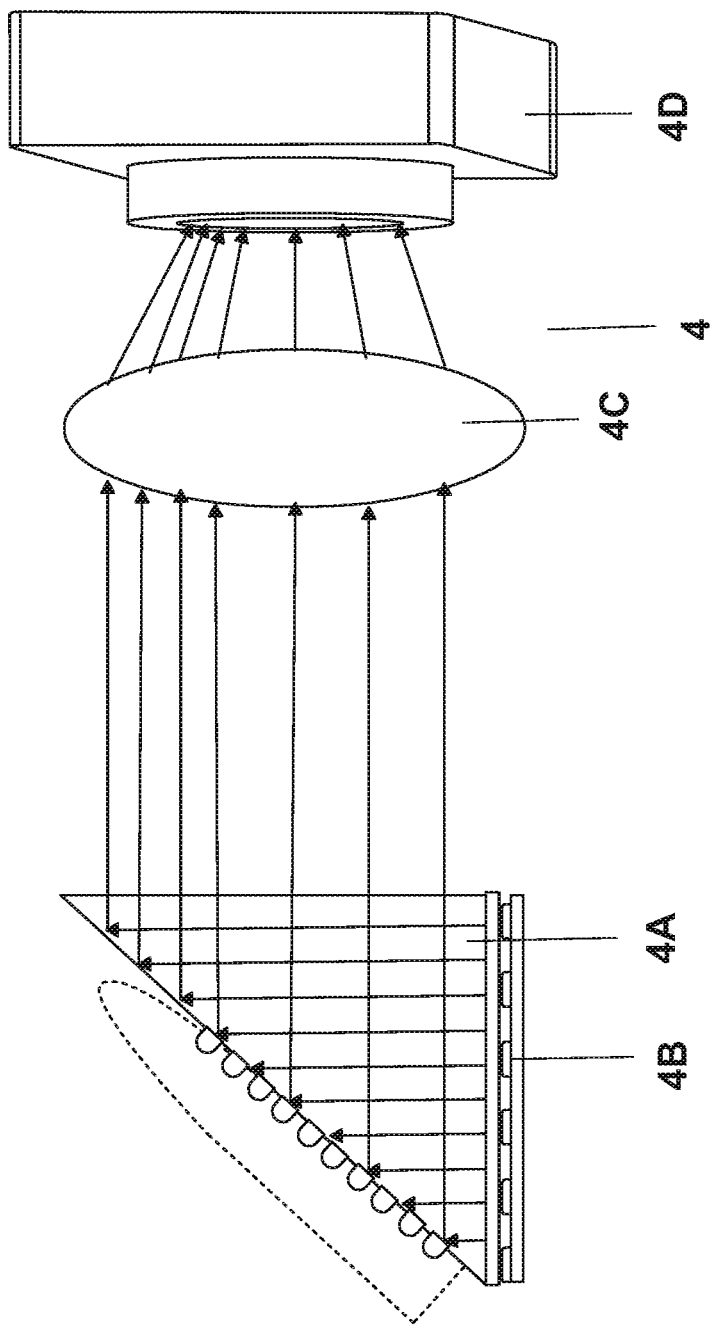

HIGH-RESOLUTION PORTABLE BIOMETRIC READER FOR NEWBORNS

The present patent of invention relates to biometric readers in general, more specifically to a high-resolution portable biometric reader for newborns which, according to the characteristics thereof, provides, as its basic principle, the creation of a biometric reader for newborns in a specific, stand-alone, curved and portable structure of electronic type and based on a frame and a comfortable handle enabling the operator to hold the reader in a single hand and arrange the capture surface area according to the newborn's position thus enabling the fingerprints of the newborn and those of the mother to be digitally captured using the frustrated total internal reflection technique with a prism as an optical system having a resolution greater than 29 lp/mm (1450 ppi) over the entire capture area of more than 18×36 mm, so as to provide, in an extremely practical, safe and accurate way, full optimization in the capturing procedures for fingerprint, palm print and footprint imaging of newborn babies and the fingerprints of the respective mothers, i.e., the simultaneous registration of the fingerprints of both the baby and the mother and the subsequent inclusion in a medical register system to improve record tracking.

With a specific design and format and easy access for adaptation and user safety, convenience features in handling and functionality very affordable and, due to its general characteristics and dimensions, easily adaptable to a variety of newborn babies, locations, and users in general, regardless of the characteristics that they may present.

Civil identification is the first step for citizenship because, as a citizen, a person is acknowledged as having rights and duties in a society. Registry offices, however, are currently the weakest link in the national identification system. Birth certificates do not ensure uniqueness to the citizen as they lack provisions binding the document to its bearer.

According to data from the UN, after drugs and weapons trafficking, human trafficking is the most profitable branch of organized crime, especially children and adolescents as well as babies right after birth. Official surveys from different governments show trafficking route maps.

There are proven facts of illegal organ trafficking in several regions in Brazil, as well as people disguised as social assistants who try to convince poor pregnant women to hand it their babies as soon as they are born; requests for the identification of children found with suspect women are quite common, as well as those children whose mothers' names in the Certificate of live birth are different.

Though provided in the Brazilian law, Law no. 8069/90—Children and Adolescents Statute, the current newborn identification system is outdated, thus making identification impossible and bolstering children trafficking, organs trafficking, exchange of babies and ideological falsehood crimes, as it does not contain provisions to properly identify children and create a link connecting the child to the information contained in the birth certificate or to the legal guardians.

Current mechanism to collect footprint from a newborn, using ink and paper, is not effective and cannot be used to collect palm print and fingerprint since the newborn could put their hand, dirty with ink, to their mouth. Quality of such collection is not assured as it depends on human effort and due attention to the matter is not always guaranteed. Besides, resolution of the images obtained with the ink and paper collection method do not provide enough details for proper visualization of newborns' fingerprints.

The use of papilloscopic images is more attractive than other types of biometrics, as they are not invasive, provide easy application and acceptance, besides the large advantage of immutability that allows their use in future identification. Nevertheless, collection of such images in newborn babies becomes a difficult process since papillary crests in babies are, in average, 2.5 to 3 times smaller than in adults and are more susceptible to deformation.

Nowadays, commercially available biometric systems are fully used for the identification of adults. Even considering the fast-growing evolution of biometric technologies, few approaches have been developed for neonatal identification. That means ignoring about a hundred and thirty-one million annual births taking place worldwide. The problem is even bigger if the world population of children between zero to five years old, about five hundred million, is taken into consideration.

The reality is that, despite maturity of fingerprint-based technologies, there is no biometric system in the world capable of identifying newborn babies, i.e., the lack of such technology justified such a failure. The technological gap is not an issue anymore; the excuse to subject children to vulnerability and insecurity regarding identification is no longer acceptable.

The use of biometric readers has flourished in the last few years with several applications related to user identification. Said readers capture fingerprint images and are coupled to software programs that recognized them and identify the individual possessing said fingerprints. Examples of such readers can be found in cash machines, banks, electronic clocking systems and patient registration systems.

It should be noted that, for the fingerprint identification and registering system to be efficient and robust, the images captured need to meet determined resolution and sharpness standards. For instance, FBI provides in its legislation that biometric readers certified for identification must have a minimum resolution of 500 ppi and 1000 ppi for fingerprint registration. Despite being enough for capturing good images and solving details of adult fingerprints, these resolution values are not true for newborns, whose fingerprints and other details are significantly smaller than those of adults.

It should also be noted that, the shape of the device used for capturing babies' fingerprints and footprints is also important, since the user needs to hold and position the device in the adequate position with a single hand while arrange the fingers, hands, or feet of the baby on the contact surface, with the proper orientation and pressure for a good quality image capture. One of the most important aspects of the device shape is the way in which the user picks it up so as to hold it in an adequate and safe way to make it easier to handle it and reduce the risk of falls. An optimized handle reduces the possibility of injuries during the job, such as the repetitive strain injury and osteoarticular diseases related to the job.

In this line of action, it has become essential for families and government agencies the invention of a device capable of generate a link between a newborn child and its mother during birth and within the delivery environment, as it would represent a big step in the prevention of children going missing, as well as helping recover and identify them. Besides, such a device would allow for medical registration and efficient follow-up of treatments, including vaccination schedule, thus resulting in a better care and health for newborns.

In an extensive review of the literature in order to provide the current state of the art of biometric readers, more specifically biometric readers for newborns in general, object of the present patent of invention, documents relevant to the prior art related to the specific object claimed in the present invention were not described, namely, a portable biometric reader that can be held with a single hand and with a minimum required resolution of 1450 ppi over an minimum area of 18×36 mm, and that could be used for the fingerprint imaging of newborn babies; however, a brief description of some documents in the literature and of patents are due for a perfect interpretation of the intended technical field.

Within the context of literature, the article by Koda, Higuchi, and Jain (Advances in Capturing Child Fingerprints: A high Resolution CMOS Image Sensor with SLDR Method, BIOSIG 2016, page 329), the authors describe a device capable of producing images with a resolution of 1270 ppi and show that it is capable of distinguish the crest valleys of newborns fingerprints, as shown in FIG. 6 from the article. However, in this figure, as well as in the figures from a prior article (Jain et al., Fingerprint Recognition of Young Children, IEEE Transactions on Information Forensics and Security, vol. 12, page. 1501, 2017), an image with the pores occurs only from the third month of life on, thus making it difficult the unique identification of the child.

In the context of patents, there are a large number of them in the area of fingerprint biometric readers, but most of them claim the method of image Generation (FTIR or scattering), optical architecture, the use of the special components for reducing distortions and the use of films to improve the quality of the image. In all the patent documents found, however, none deals with the application for the Generation of a proper image for baby fingerprint and their requirements, i.e., a resolution greater than 1450 ppi over an area higher than 18×36 mm (minimum area for imaging of palm print and footprint regions with greater information), portability and usability.

Besides the fact that none of these patents claim the handle, as claiming a piece of equipment with compact structure, easy hygiene, and practical assembly, designed for optimal productive processes, with an ideal handle for use in ergonomic aspects and focused on the best user experience (biometry collector and agents collected), that is, designed with high onboard technology that allows easy adaptation to the universe of hospitals and maternity homes.

In the specific case of the US patent document US20050169506, a portable and lightweight device for large format fingerprint has been described, involving the capture of four or more fingers in adults with a capture surface larger than 3×3", much larger than the one required for the fingerprint of babies and with no discussion on resolution.

The overall design of the present high-resolution portable biometric reader for newborns, object of the present patent of invention, is entirely based on its simple and robust structure with a minimum required number of components and extremely simple, safe and optimized operation, combined with fairly practical manufacturing and maintenance procedures so as to generate a practical and efficient biometric reader for newborns for fingerprint imaging of newborn babies capable of being held in a single hand by means of a frame with a transparent surface for capturing images of fingers, hands, or feet of newborn babies and an optical system with a minimum required resolution of 29 lp/mm (1450 ppi) over an entire minimum capture area of 18×36 mm organized in the inner core of the frame.

In a more specific way, the biometric reader for newborns allows the simultaneous registration of both the baby and the mother's fingerprints so as to ensure the link of a newborn baby to its mother from the first minutes of its birth, still in the delivery room, by means of the fingerprint biometry of the ten fingers, palm print and footprint of the baby and the fingerprint biometry of the ten fingers of the mother. As a consequence, said biometric identification and bond ensure the generation of the baby's identification documents such as the birth certificate, civil identification register, passport and so on, as well as the control of the physical access to maternities, thus ensuring babies are not kidnapped or exchanged, and helping recover and identify missing babies and children.

It should be noted that the biometric reader for newborns was designed with curved shapes for a better adaptation to the human body, presenting an ideal size for rough and continuous handling by doctors and nurses alike, thus avoiding job-related osteomuscular injuries (DORT). Besides that, biometric data is easier to read due to slanted capture surface that allows doctors and nurses to directly place the equipment in an ideal position according to the baby's position.

The present patent of invention is based on the application of components and processes in a differentiated concept to meet the several requirements the nature of its use demands, that is, fingerprint, palm print and footprint imaging of newborn babies (neonates). The concept ensures a biometric reader for newborns of great efficiency, functionality, strength, durability, safety, versatility, accuracy, economy due to the excellent aggregate technical qualities, which provide advantages and improvements in the fingerprint, palm print and footprint imaging of newborn babies (neonates) and fingerprint imaging of respective mothers and whose general characteristics differ from the other shapes and models widely known in the current state of the art.

The present patent of invention comprises the use of a modern, efficient, safe and functional high-resolution portable biometric reader for newborns formed by a set of properly incorporated electronic and biometric solutions, forming a complete and differentiated biometric reader for newborns with exclusive design, great finish details and specific characteristics, which incorporates its own specific and proper structure of electronic type of high durability and strength, ergonomic shape and containing a properly integrated and symmetrically arranged between each other a frame as a structural element and a comfortable handle for holding the device in a single hand, and a core as a storage element for the optical and electro-optical components for fingerprint imaging in order to make it possible to form a single, complete and safe assembly, whose shapes and internal and external arrangements enable seamless adaptation to several different types of operators, newborn babies and mothers, and specially designed for these purposes.

The present biometric reader for newborns is based on the application of components and processes in a differentiated design without, however, achieving a high degree of sophistication and complexity, thus making is possible to solve some of the main drawbacks of other shapes and models known in the state of the art and employed in the procedures for fingerprint, palm print and footprint imaging of newborn babies (neonates), which are located in an operating range in which are very common the limitations on use and application, low efficiency and performance, frequent accidents of different severities, the shapes and models are either based on simple adaptations, thus producing high insecurity, great wear and fragility, low durability and strength, low versatility, high inaccuracy, laborious application, no ergonomics, low efficiency and performance, or they have a large size thus resulting in a high cost, general high volume and weight, little flexibility, high maintenance, great waste of time and complex manufacturing process.

The objectives, advantages, and other important characteristics of the patent of invention in question can be more easily understood when read in conjunction with the accompanying drawings, in which:

FIG. 1A is a perspective view of the high-resolution portable biometric reader for newborns.

FIG. 3 is a diagram view of the high-resolution portable biometric reader for newborns showing the finger application on the prism.

Figure 1B:
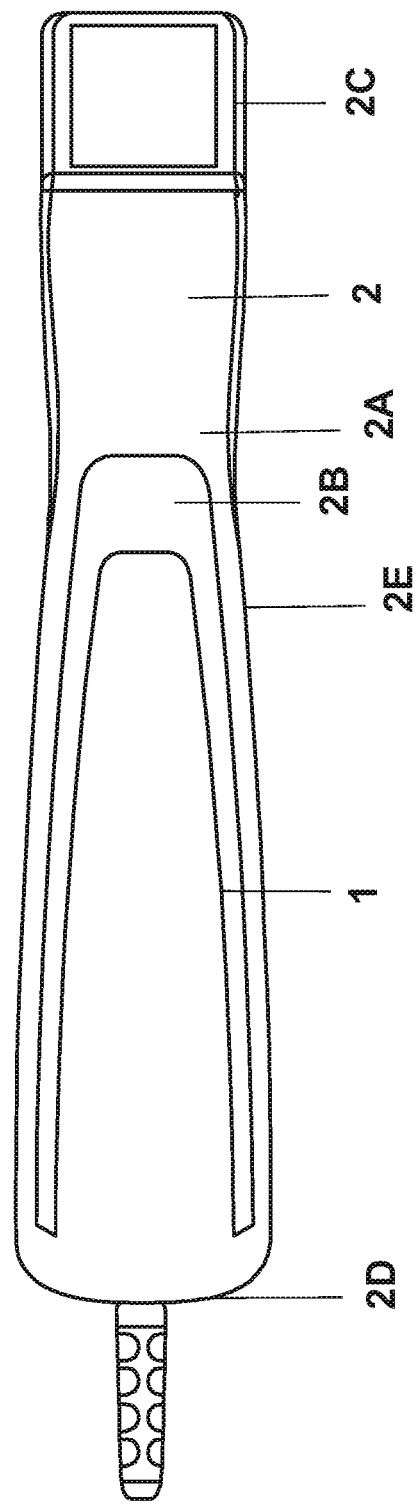
FIG. 1B is a top view of the high-resolution portable biometric reader for newborns.
Figure 1C:
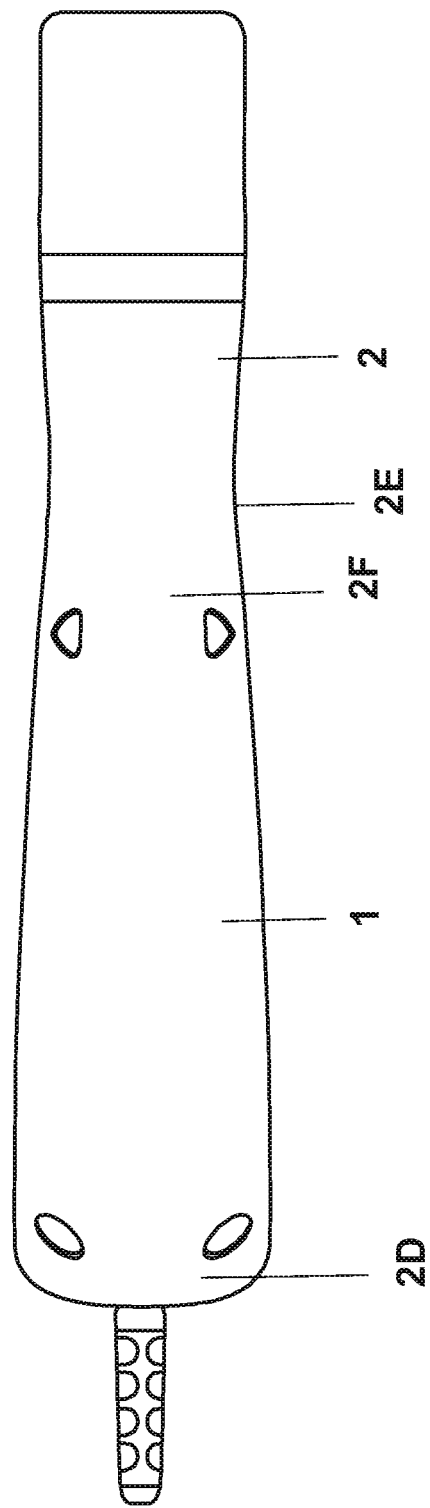
FIG. 1C is a lower view of the high-resolution portable biometric reader for newborns.
Figure 1D:
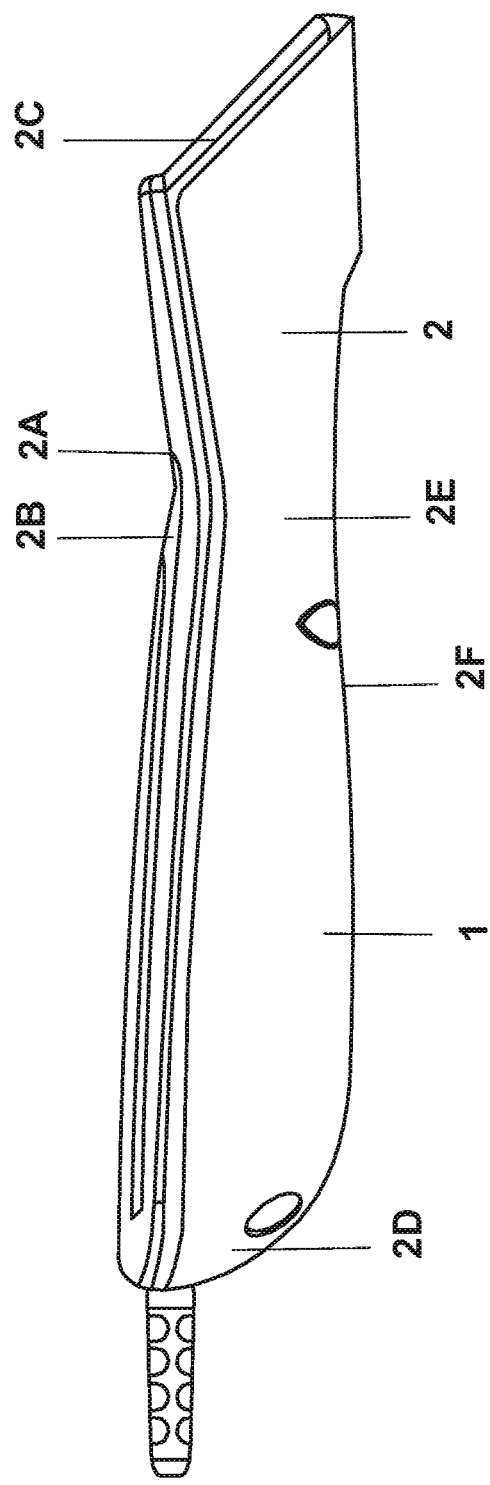
FIG. 1D is a right-side view of the high-resolution portable biometric reader for newborns.
Figure 1E:
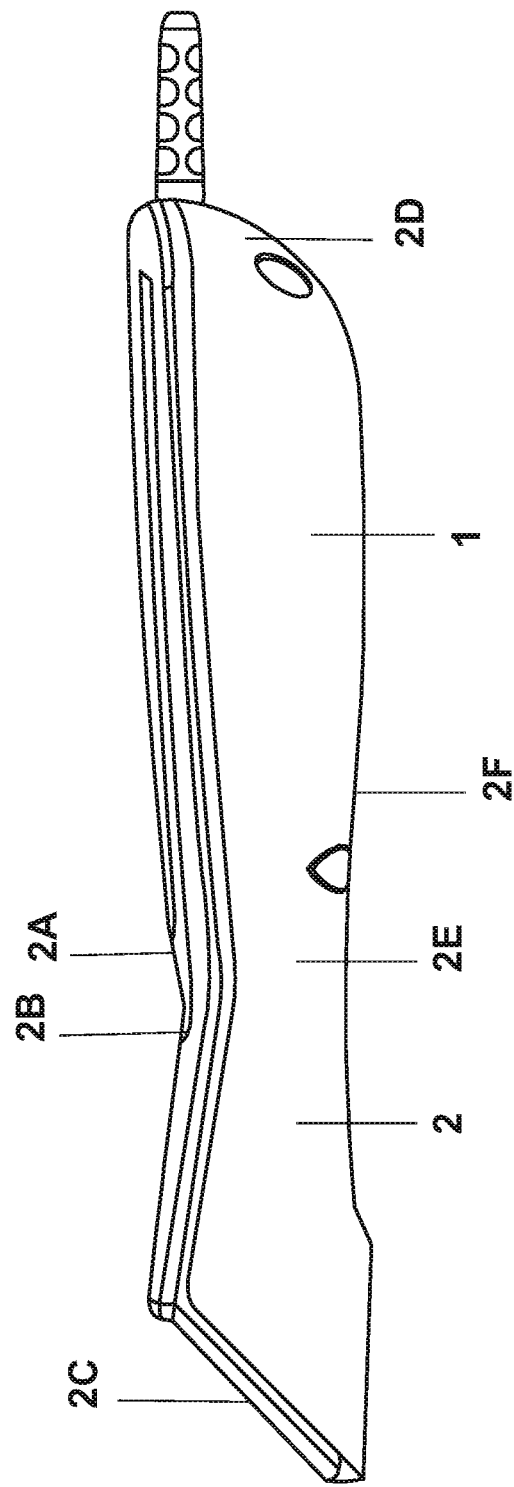
FIG. 1E is a left-side view of the high-resolution portable biometric reader for newborns.
Figure 1F:
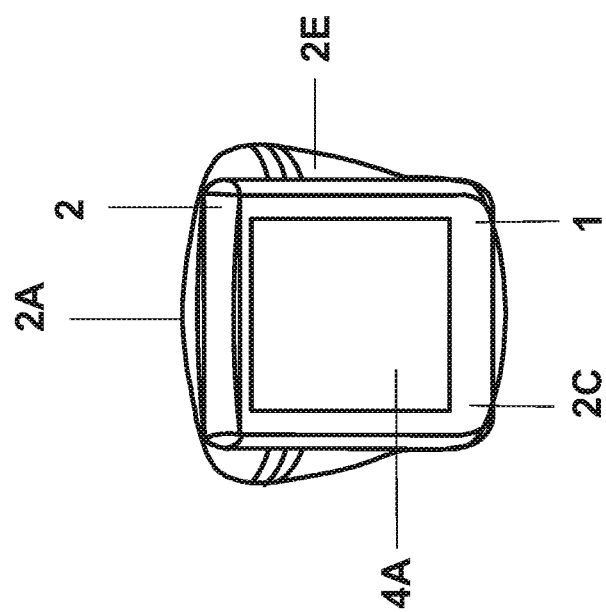
FIG. 1F is a front view of the high-resolution portable biometric reader for newborns.
Figure 1G:
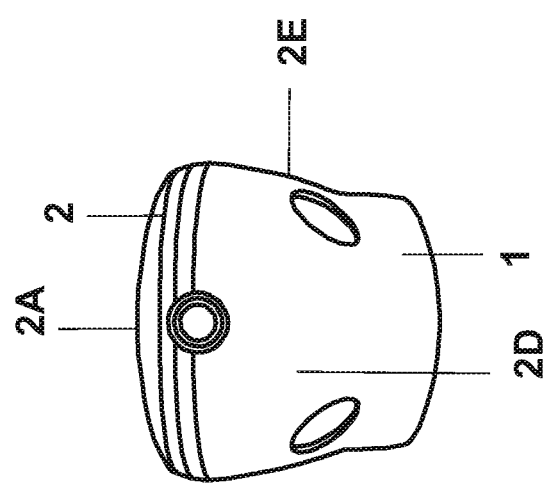
FIG. 1G is a rear view of the high-resolution portable biometric reader for newborns.
Figure 2A:
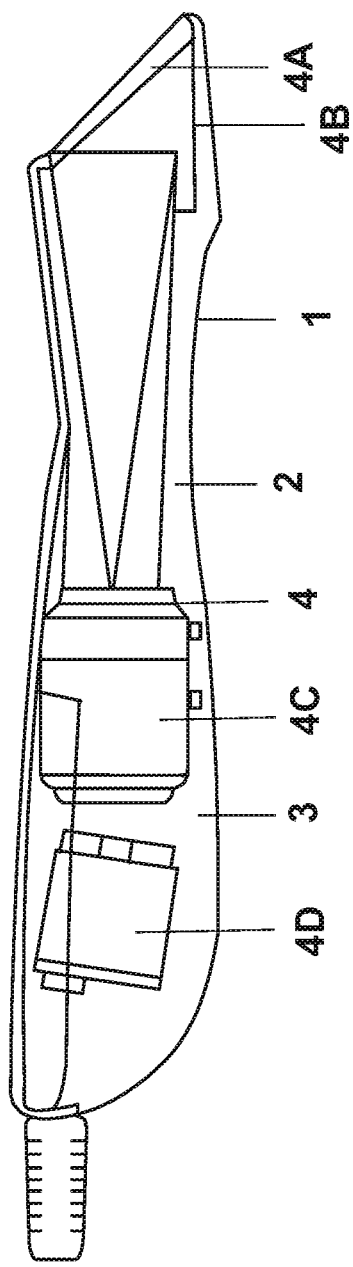
FIG. 2A is a cross-section side view of the high-resolution portable biometric reader for newborns.
Figure 2B:
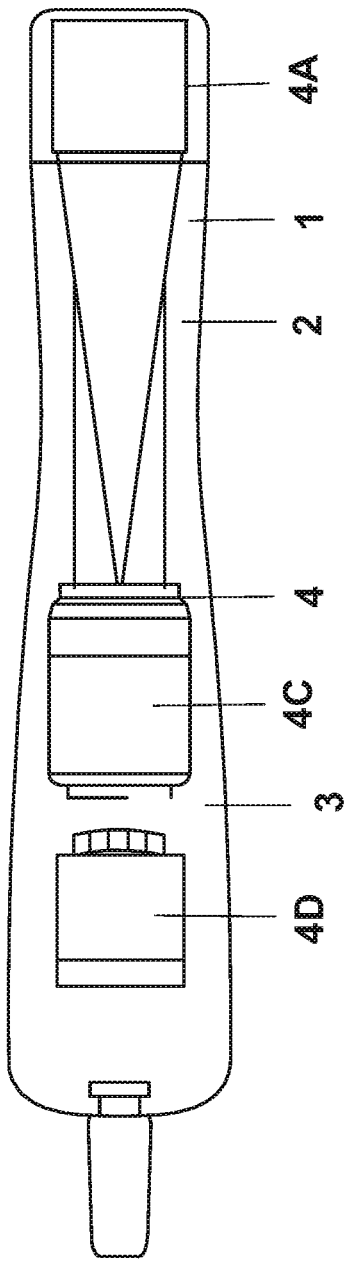
FIG. 2B is a cross-section top view of the high-resolution portable biometric reader for newborns.
Figure 4:
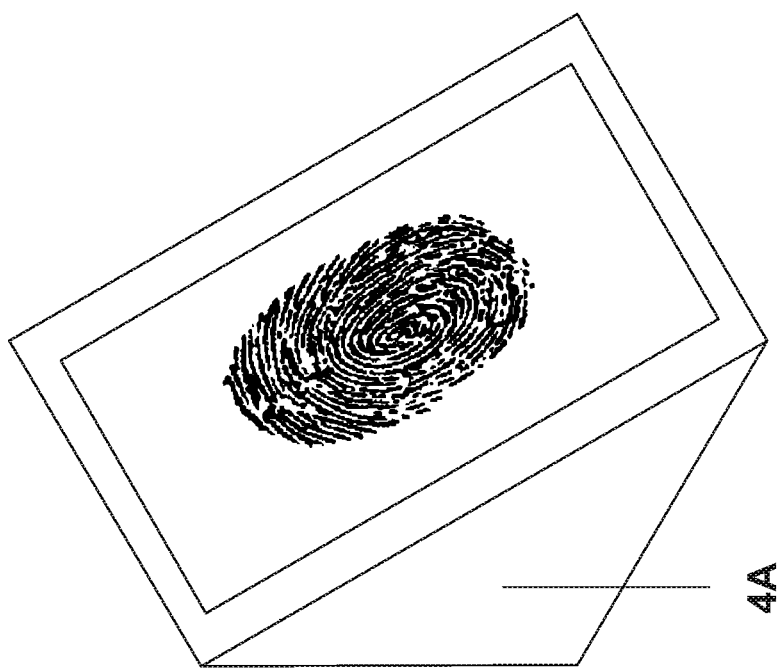
FIG. 4 is a perspective view of the fingerprint in the high-resolution portable biometric reader for newborns.
Figures 5A, 5B:
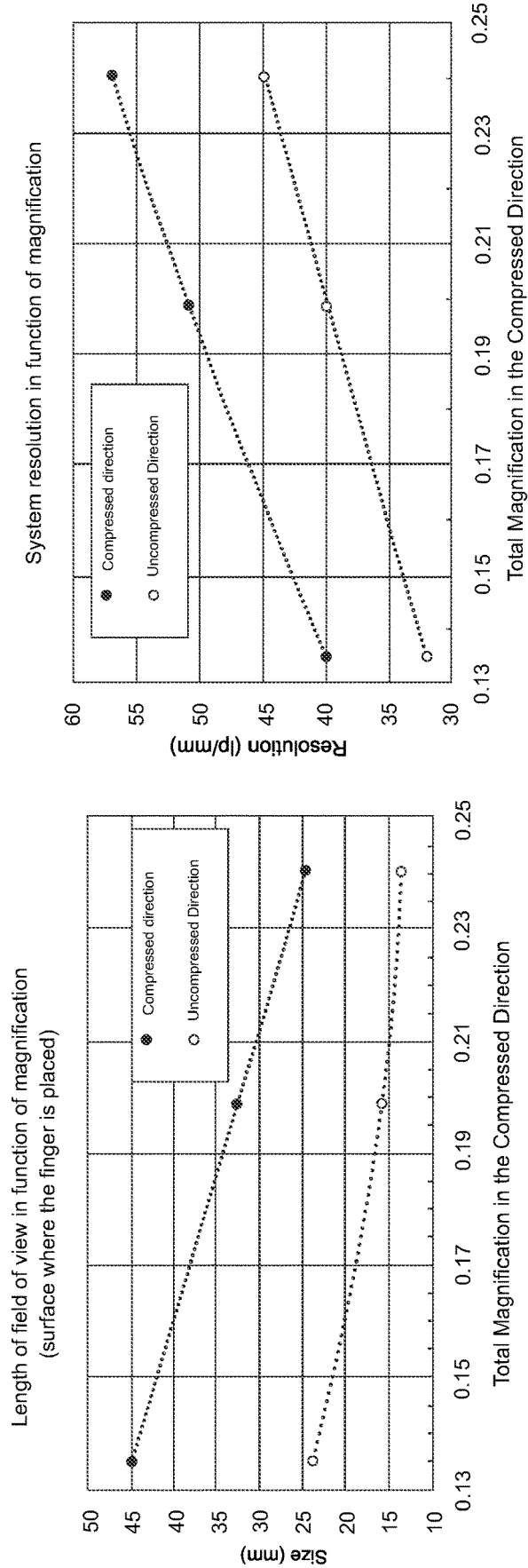
FIG. 5A is a chart of the capture area size of the high-resolution portable biometric reader for newborns tested in function of the total magnification in the image compression direction by the prism—length of field of view in function of magnification (surface where the finger is placed).
FIG. 5B is a chart of the system resolution in the capture area of the high-resolution portable biometric reader for newborns tested in function of the total magnification in the image compression direction by the prism—system resolution in function of magnification.
Figure 6:
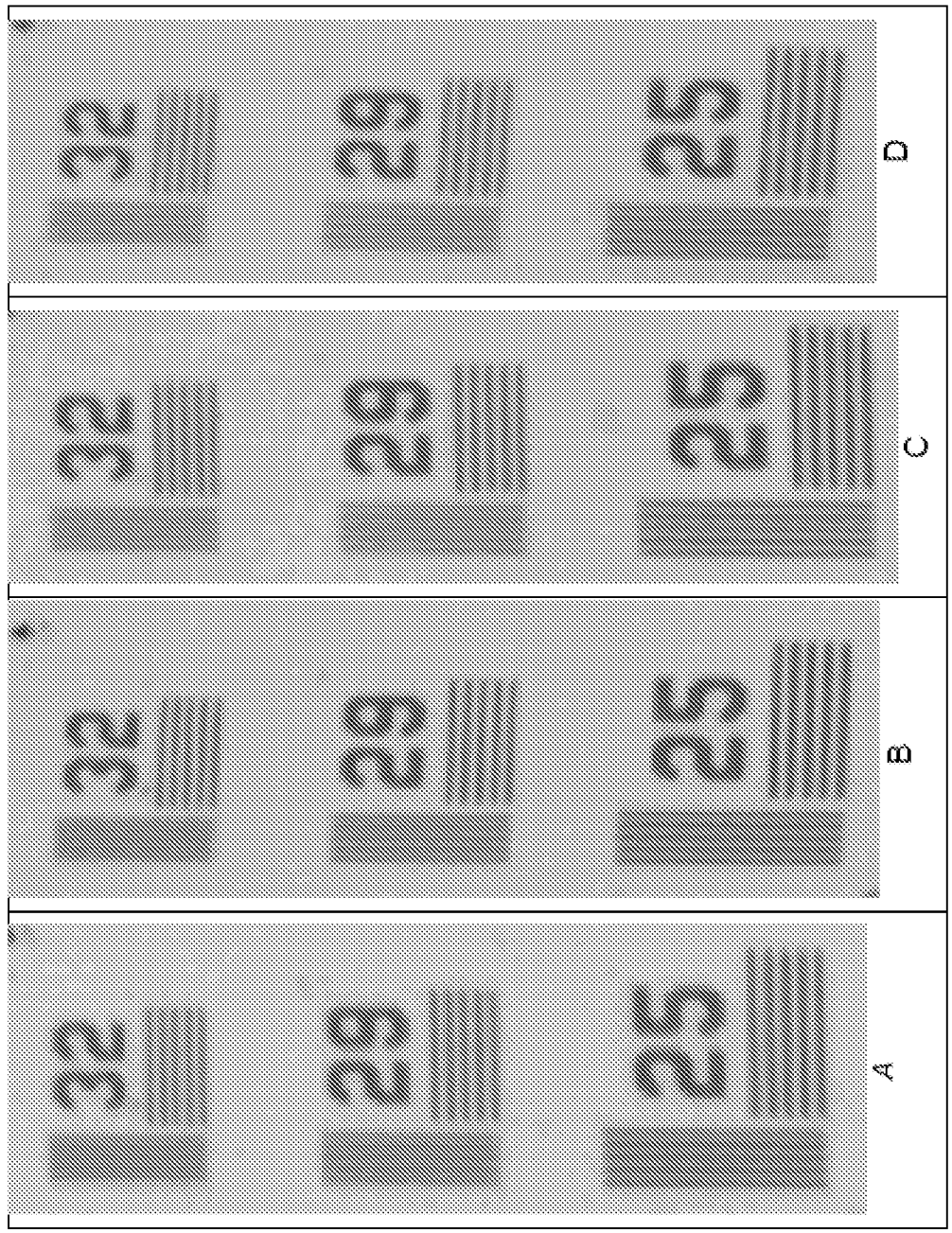
FIG. 6 are images of the NBS1963A test target at the prism edges for a total magnification in the compressed direction of 0.17: A—left-hand upper corner. B—right-hand upper corner, C—left-hand lower corner, D—right-hand lower corner.

As shown from the accompanying drawings that illustrate and integrate the present descriptive report of the patent of invention "High-Resolution Portable Biometric Reader for Newborns", FIG. 1A) shows the biometric reader in general comprising a biometric reader for newborns (1) complete and with specific characteristics, incorporating its own proper and specific portable structure of electronic type, of high durability and strength, ergonomic shape with internal and external shapes and arrangements that adapt to the various types of operators, newborn babies and mothers, and containing a properly integrated and symmetrically arranged between each other a frame and a comfortable handle (2) and a core (3) for the optical and electro-optical components for fingerprint, palm print and footprint imaging of newborn babies and the fingerprint imaging of the mother by means of an optical system (4) using the method of frustrated total internal reflection with a prism with a resolution greater than 29 lp/mm (1450 ppi) over the entre capture area and over a capture area higher than 18×36 mm, being the set connected to a handheld computer for treatment, storage and transmission of images.

42 The frame and the handle (2) is comprised by a V-like shaped upper recess (2A) arranged along the entire length of the upper surface of the frame (2); a horizontally U-like shaped upper recess (2B) horizontally, parallely and symmetrically centered in the upper rear portion of the frame (2); a rectilinear front edge (2C) slanted and symmetrically arranged along the entire length of the front surface of the frame (2); a convex rear curve (2D) symmetrically arranged around the lower rear portion of the frame (2); two concave side recesses (2E) vertically and parallely arranged along the entire length of the side surfaces of the frame (2); and a concave lower recess (2F) arranged along the lower rear portion of the frame (2).

The optical system (4), shown in FIG. 3, is comprised by a right angle three-sided glass prism (4A) vertically, parallelly and symmetrically arranged along the entire length of the rear surface of the frame and handle (2); a green LED panel (4B) of parallelepipedal shape and horizontally, parallelly and symmetrically arranged under and along the entire length of the lower surface of the right-angle three-sided glass prism (4A)—in front of the right-angle cathetus; an internal objective lens (4C) with 25 mm focal length, maximum size ⅔", minimum working distance of 100 mm, axis resolution of 200 lp/mm and edge resolution of 160 lp/mm and vertically, parallelly and symmetrically spaced away from the rear surface of the right-angle three-sided glass prism (4A); and an image sensor (4D) vertically, parallelly and symmetrically spaced in the rear surface of the internal lens (4C).

The right-angle three-sided glass prism (4A) is lightened by the green LED panel (4B) arranged close to the cathetus surface of the right-angle three-sided glass prism (4A). Light emitted by the green LED panel (4B) suffers total internal reflection in the hypotenuse surface in the right-angle three-sided glass prism (4A). When a finger touches that surface the fingerprint crests, provided with an index of refraction close to that of the right-angle three-sided glass prism (4A), frustrate that total internal reflection and the incident rays on these points are no longer reflected by the right-angle three-sided glass prism (4A). The rays that were reflected by the right-angle three-sided glass prism (4A) are captured by the internal lens (4C) and imaged by the optical image sensor (4D).

More specifically, the optical system uses a right-angle three-sided glass prism (4A) of ninety degrees, the generated image is compressed in the direction of the cathetus of the right-angle three-sided glass prism (4A), that is, introduces a magnification of 0.707 in that direction. Thus, the optical system total magnification will be 0.707 times the internal lens (4C) magnification in that direction of compressed image and equal to the internal lens (4C) magnification in the direction without compression.

The high-resolution portable biometric reader for newborns is based on images, regardless of the method used as optical system, that is, it covers from the frustrated internal reflection method, scattering method, a combination of these two former methods, prism readers or no-prism readers, and even direct imaging without the use of lens.

The resolution greater than 29 lp/mm (1450 ppi) over the entire capture area refers to the resolution in the object plane, that is, in the transparent surface where the fingers, hands and feet of newborns and the fingers of mothers are placed. The resolution in the image plane, that is, the resolution in the image sensor ($R_{image}$) is equal to the resolution in the object plane ($R_{object}$) divided by the magnification of the optical system (M), which, according to the present invention ($R_{object}$) is greater than 29 lp/mm and M is equal to the sensor size divided by the object size, where the object size corresponds to the size of the fingerprint capture area in the transparent surface in which the fingers, hands and feet of the newborn and the fingers of the mother are placed. Likely, the capture area big enough for imaging not only the fingerprints but also palm print and footprint of the baby and the fingerprints of the mother was estimated based on the size of the newborn hands published in the article by Honore, Rakza and Deruelle (*Hand measurement data from human babies at birth, from 26 to 41 weeks estimated gestational age*, published in Data in Brief vol. 7, page. 1451, 2016) that indicates the width is typically smaller than 36 mm.

The requirement provided by the equation in the image sensor resolution ($R_{image}$) refers to the complete optical system and, in order to be met, all the optical system components need to have a resolution greater than or equal to that requirement, that is, they need to have a resolution or MTF (modulation transfer function) greater than $R_{object}/M$. It is important to observe that optical architectures using prisms may present a magnification and, consequently, a resolution, different for image height and width. In this case, the requirement provided by the equation in the image sensor resolution ($R_{image}$) must be met by both sizes.

Magnification value is the value of the magnification for image capture with a width of 36 mm by the side with a larger size (sensor width) calculated by the equation of the optical system magnification (M). It is important to observe that the magnification and resolution values are the values resulting from the combination of all optical elements in the system, which may include lenses, prisms, and filters. Larger-sized sensors require an optical system with a smaller resolution, but also require lenses with a larger image circle.

The operation of the high-resolution portable biometric reader for newborns is based on a fingerprint registering process for the mother, which may be carried out as early as in the pre-natal stage or the day the mother goes to the hospital to give birth. From the mother's biometric registration, the newborn registration is carried out as follows: just after cutting the umbilical cord and the baby's first vital signs procedures still in the delivery room, a professional responsible for collecting the data cleans the baby's palms and feet and starts the fingerprint, palm print and footprint imaging procedures using the biometric reader for newborns. A specific computer program analyses the quality of the images in real time and automatically saves the data with acceptable quality, thus linking said biometry with that of the mother along with the number of the certificate of live birth. This information is stored in a database with automatic communication with the Identification Register Institute and all collected data are transmitted for the purposes of storage, authentication, validation, and identification. The maternity home or hospital, in turn, can control the newborn baby release with their mother by means of a computer program.

As a test for the biometric reader for newborns, the captures image resolution was measured by using a NBS1963A test target in the prism surface where the fingerprint is placed, object plane resolution (where the finger is placed) in the center of the prism in face of the total magnification in the compressed direction so that magnifications are smaller than 0.17, the resolution in the compressed direction is greater than 36 lp/mm, that value being higher than the minimum required value of 29 lp/mm because the object lens used has a resolution in the center region greater than 200 l/pmm, a value that is higher than the minimum of 170 lp/mm previously determined.

As the specification for the lens resolution on the objective lens edge used is drops to 160 lp/mm, the resolution in on the prism edges were also measured, where the resolution in the direction of compression is reduced to 29 lp/mm, thus meeting the conditions claimed in the present patent of invention.

As the high-resolution portable biometric reader for newborns has fully integrated components, it can be assembled and disassembled quickly, nothing comes loose or breaks off, and a high performance and efficiency is achieved, combined with high durability and complete safety during use. Once fully integrated, the components are completely locked and united, thus preventing them from loosening when in use, making the assembly fully available for the procedures of fingerprint, palm print and footprint imaging of newborn babies (neonates) and fingerprint imaging of the respective mothers in the delivery room. The biometric reader for newborns (1) can be thus used without concerns of any nature, mainly regarding the safety and durability of its components, as well as the safety of its users—operators, mothers, and newborns.

The high-resolution portable biometric reader for newborns features as specific advantages: full portability that allows it to be taken to the mother's bed and the baby's crib; high ergonomics with a shape and weight that allows it to be held and operated by the operator with a single hand in a comfortable and safe way, so that the operator's other hand is free to hold and properly position the baby's fingers, hands or feet; high resolution over the entire capture area enabling fingerprint imaging of newborn babies who are significantly smaller than those of adults; a capture area that is sufficiently large to capture an image of the significant parts of the baby's hands and feet to allow its identification; and hygienic surfaces that allow the reader's surfaces that come into contact with the baby and the mother to be cleaned and sanitized between uses.

In view of the foregoing, the biometric reader will be well received by newborn babies' parents, hospitals, government health and security agencies in general, since the high-resolution portable biometric reader for newborns has many advantages, such as: great safety, reliability and flexibility in its application; great efficiency and performance in its application due to its general conception; great comfort, convenience and safety for the users; great overall strength and durability, combined with low or no wear of the assembly as a whole; fully accessible costs which provides an optimum cost-benefit ratio; practical and safe use by any users; high range; very low and practical general maintenance; perfect and direct adaptation to different types of newborns in general; high operational accuracy; fully compatible general weight and dimensions; high ergonomics; fully hygienics; seamless integration with computer systems; and the certainly of having a biometric reader for newborns that fully meets the current rules and regulations required to its application.

All such attributes classify the high-resolution portable biometric reader for newborns as a fully versatile, efficient, practical, and safe way to be applied in the procedures of fingerprint imaging of the several different types of fingerprints, palm prints, footprints of a large number of newborn babies (neonates) and those of the respective mothers, in the most varied types of environments and users, regardless of the general characteristics these may have. It is also easy to use and handle, combined to a great performance and excellent general characteristics; dimensions and quantities, however, may vary according to the general needs of each application.

The invention claimed is:

1. A HIGH-RESOLUTION PORTABLE BIOMETRIC READER FOR NEWBORNS comprising a newborn biometric reader incorporating an ergonomically-shaped portable structure of electronic type and containing integrated and symmetrically arranged between each other a frame and a handle and a core for the optical and electro-optical components for fingerprint, palm print and footprint image acquisition of newborn babies and fingerprint image acquisition of mothers by means of an optical system via a method of frustrated total internal reflection with a prism having a resolution greater than 29 lp/mm (1450 ppi) over the entire capture area and a capture area of more than 18×36 mm, the set being interconnected to a handheld computer for treatment, storage and transmission of images, characterized in that the frame and handle are comprised by a V-like shaped upper recess arranged along the entire length of the upper surface of the frame and the handle; a horizontal U-like shaped upper recess horizontally, parallelly and symmetrically centered in the upper rear portion of the frame and the handle; a rectilinear front edge slanted and symmetrically arranged along the entire length of the front surface of the frame and the handle; a convex rear curve symmetrically arranged around the lower rear surface of the frame and the handle; two concave side recesses vertically and parallelly arranged along the entire length of the side surfaces of the frame and the handle; and a concave lower recess arranged along the lower rear surface of the frame and the handle; and the optical system to be comprised by a right-angle, three-sided glass prism vertically, parallelly and symmetrically arranged along the entire length of the front surface of the frame and the handle of parallelepipedal shape and horizontally, parallelly and symmetrically arranged under and along the entire length of the lower surface of the right-angle, three-sided glass prism in front of the right-angle cathetus; an internal objective lens with 25 mm focal length, maximum size $2/3$", minimum working distance of 100 mm, axis resolution of 200 lp/mm and edge resolution of 160 lp/mm and vertically, parallelly and symmetrically spaced away from the rear surface of the right-angle three-sided glass prism; and an image sensor vertically, parallelly and symmetrically spaced in the rear surface of the internal lens.

\* \* \* \* \*